United States Patent [19]

Weiss

[11] Patent Number: 4,765,334

[45] Date of Patent: Aug. 23, 1988

[54] SURGICAL DEVICE FOR PERFORMING THORACOSTOMIES

[76] Inventor: Sol Weiss, 17227 Queson Pl., Encino, Calif. 91304

[21] Appl. No.: 2,579

[22] Filed: Jan. 12, 1987

[51] Int. Cl.[4] .................... A61B 17/32; A61B 17/34
[52] U.S. Cl. ................................................ 128/305.3
[58] Field of Search ........... 128/305.3, 200.26, 329 R; 604/159, 164

[56] References Cited

U.S. PATENT DOCUMENTS

| 300,285 | 6/1884 | Russell | 128/305.3 |
| 2,840,082 | 6/1958 | Salvatore | 128/305.3 |
| 3,688,773 | 9/1972 | Weiss | 128/305.3 |

*Primary Examiner*—Michael H. Thaler

*Attorney, Agent, or Firm*—Gerald L. Price

[57] ABSTRACT

An improved surgical device for performing thoracostomies. The device includes a holder for a curved stylet or a flexible tube and curved stylet combination which holder includes a two piece curved needle attached to a pair of handles, each handle including one part of the needle, which handles can be spread apart for insertion of a curved stylet or tube and curved stylet combination between the needle parts. When it is desired to remove the device from the patient, one of the handles having its needle part can be removed from the other handle having its needle part without disturbing the tube or stylet alone held between the needle parts. In this manner, sutures can be easily made in a chest or drainage effected in carrying out a thoracostomy.

8 Claims, 2 Drawing Sheets

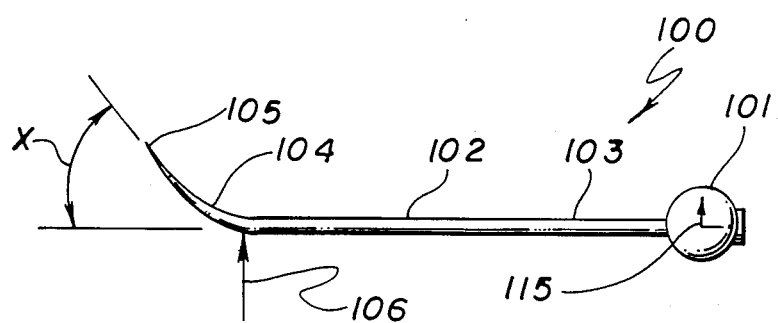
FIG. 3
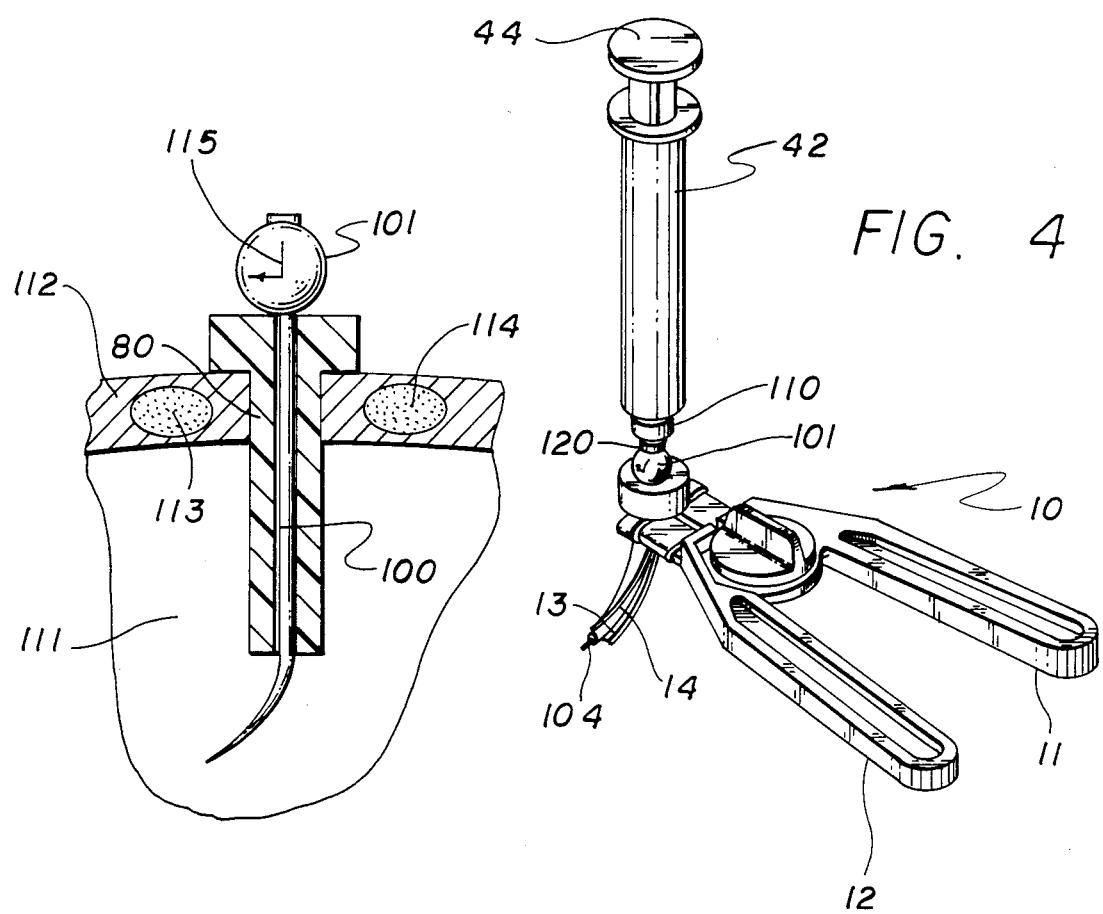
FIG. 4
FIG. 5

SURGICAL DEVICE FOR PERFORMING THORACOSTOMIES

BACKGROUND OF THE INVENTION

1. Field of the Invention

The invention relates to surgical devices; and, more particularly, to a curved stylet and holder therefore for use in thoracic applications.

2. Description of the Prior Art

Various types of surgical devices are known in the prior art. In my copending application Ser. No. 701,914, filed Feb. 14, 1985, now U.S. Pat. No. 4,643,188, I describe and claim a number of such devices, certain of which are useful in thoracic applications. In such operations, the surgeon makes a cut in the side of the body between the ribs. A conventional trachar is used to make this cut. In thoracic operations, it is critical that the surgeon get into the pleural cavity of the patient which lies under the ribs. In doing so, surgeons use their finger to guide the trachar so as to get it into the pleural cavity. However, if the blood of the patient is contaminated and the surgeon's finger is cut, the finger would get infected. This is of course of serious concern to the surgeon, particularly in view of the discovery in recent years of certain disease from contaminated blood where the patient may be a carrier and appear to be in good health.

There is thus a need for surgical devices wherein the slit made with a trachar in thoracic operations can be explored using instrumentation to locate the pleural cavity.

SUMMARY OF THE INVENTION

It is an object of this invention to provide a surgical device for locating the pleural cavity during thoracic operations.

It is still further an object of this invention to provide a surgical device which is adapted to be positioned in the pleural cavity to direct a tube into either the upper thorax or posterior portion of the thorax of the patient.

It is another object of this invention to provide a curved stylet adapted to be used with curved needles and chest tubes.

These and other objects are preferably accomplished by providing a holder adapted to hold a curved stylet or flexible tube and curved stylet combination which holder includes a two piece curved needle attached to a pair of handles. Each handle includes one part of the needle, the handles being spread apart for insertion of a curved stylet or tube and curved stylet combination between the needle parts. When it is desired to remove the device from the patient, one of the handles having its needle part can be removed from the other handle having its needle part without disturbing the tube or stylet alone held between the needle parts. In this manner, sutures can be carried out easily in a chest or drainage effected in carrying out a thoracostomy.

BRIEF DESCRIPTION OF THE DRAWING

FIG. 3 is a vertical view of a stylet in accordance with the invention;

FIG. 4 is a perspective view of the device of FIGS. 1 and 2 holding the stylet of FIG. 3; and FIG. 5 is an illustrative view of the stylet of FIG. 3 shown disposed in the pleural cavity of a patient.

DESCRIPTION OF THE PREFERRED EMBODIMENT

Figure 1:
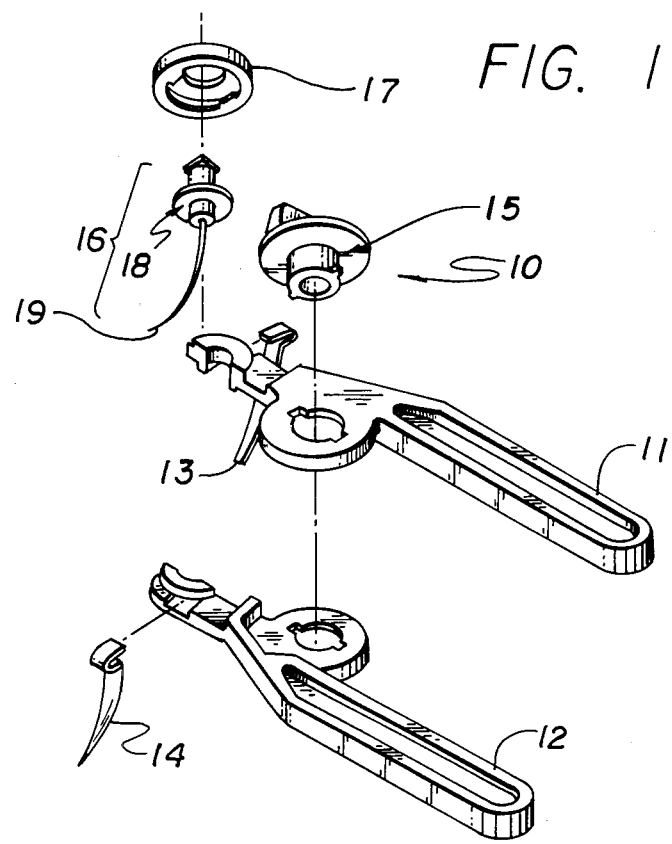
FIG. 1 is an exploded view of a surgical device useful in holding the improved stylet of the invention.

As heretofore discussed, the invention herein relates to an improved stylet particularly useful in the surgical device described and claimed in my copending U.S. patent application Ser. No. 701,914, filed Feb. 14, 1985, now U.S. Pat. No. 4,643,188, in the name of Sol Weiss, applicant herein. Applicant hereby incorporates by reference the device described and claimed in application Ser. No. 701,914. For purposes of illustration, certain figures of the drawing in application Ser. No. 701,914 are set forth herein to show the environment of the invention. However, reference should be made to application Ser. No. 701,914 for a full understanding of the device disclosed therein.

Figure 2:
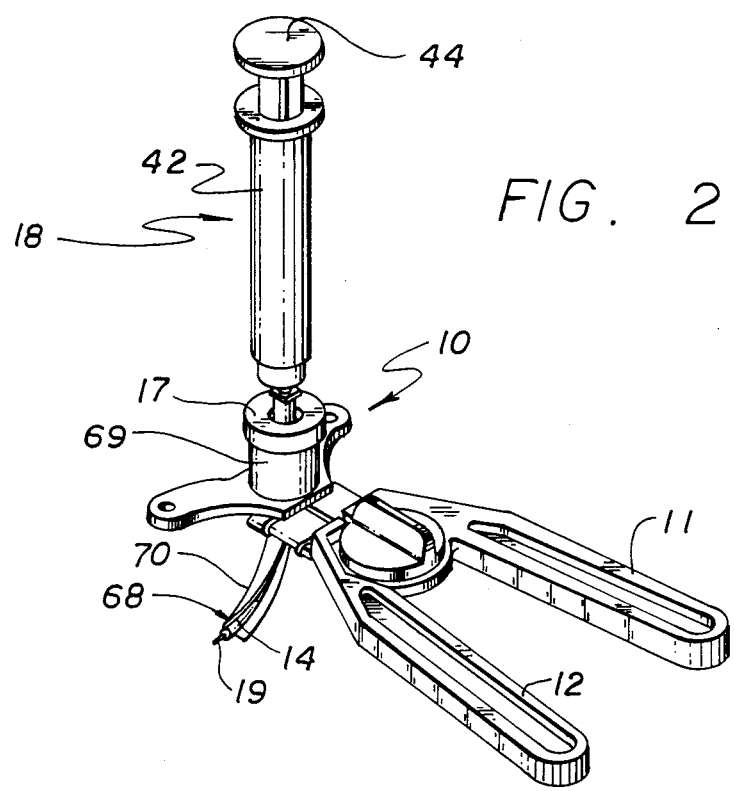
FIG. 2 is an assembled perspective view of the combination of FIG. 1 showing a tube and stylet clasped therebetween.

Thus, as seen in FIG. 1, surgical device or instrument 10 of application Ser. No. 701,914 is shown in exploded view. Device 10 includes a pair of handle portions 11,12. A pair of needle halves 13,14 are provided, each half 13,14 being adapted to be secured to its respective handle portion 11,12. A locking key 15 is provided adapted to secure handle portions 11,12 together. Stylet holder 16 is also provided comprised of a collar 17 adapted to receive therein a needle holder or stylet 18 having a needle 19 included therewith. The foregoing is a brief description of the parts of device 10 and the final assembled position thereof is shown in FIG. 2 (FIG. 20, of application Ser. No. 701,914). Again, reference thereto should be made for a complete description of the elements of FIGS. 1 and 2 and the assembly of the same. As seen in FIG. 2 herein, and as shown in application Ser. No. 701,914, a syringe 42, with an 44, is assembled to stylet 18. Needle 19 is shown as inserted into a tube 68 clamped between needle halves 13,14. Tube 68 has an upper cylindrical portion 69 and a lower cylindrical portion 70, all as disclosed in application Ser. No. 701,914 with respect to FIG. 20 therein.

The device 10 of FIGS. 1 and 2 can be used to carry out thoracostomies. As particularly contemplated in the present invention, as seen in FIGS. 3 to 5, the stylet 19 of FIGS. 1 and 2 is replaced by a stylet 100. Stylet 100, FIG. 3, has a ball shaped connector 101 at one end and an elongated body portion 102, which may be hollow, extending therefrom. Body portion 102 includes a first straight linearly extending body section 103 and a second curved end section 104 terminating in a sharp tip 105. The curved end 104 makes an angle x with a line extending through straight section 103 and curved end 104. The junction of section 103 with section 104 is indicated by the arrow 106.

As seen in FIG. 4, the stylet 100 is curved to conform generally to the curve in the needle halves 13,14 of the device of FIGS. 1 and 2 and, although it can be used without needle halves 13,14 as will be discussed, it is particularly useful with such halves.

Thus, in use, the stylet 100 in FIG. 4 is inserted between needle halves 13,14 and used to cut the skin level of the patient. A conventional leur adapter 120 (FIG. 4) is connected to ball connector 101 with syringe 42 and obdurator 44 of FIG. 2 connected thereto as is well known in the art. The free movement of the obdurator 44 in syringe 42 would indicate the proper depth of penetration into the pleural cavity as discussed in my copending application.

After such penetration, which is determined using the stylet 100 and thus substitutes for the surgeon's finger, the stylet 100 is withdrawn and it is now desired to place a drainage tube into the pleural cavity. As discussed heretofore in my copending application, the tube is inserted down between the needle halves while the halves remain in the patient to maintain the proper depth of penetration. In place of the stylet of my copending application, stylet 100 is placed in the tube or the tube is pushed over the stylet and the tube, with the stylet 100 therein, is guided down between the needle halves. The final position of tube 80 and stylet 100 is shown in FIG. 5 (needle halves 13,14 having been removed in the manner discussed in my copending application). Thus, as seen in FIG. 5, tube 80 has stylet 100 disposed therein, the curved stylet providing rigidity to the flexible thoracic tube 80.

Stylet 100 may be of metal or plastic or any other suitable material. The curvature of stylet 100 aids in directing tube 80 into the proper location within the chest cavity. However, the degree of curvature x is between about 5 to 55 degrees, with an angle of 35 degrees being preferred Further, if the overall length of body portion 102 is 17 inches or 43.6 cc long, the curved end 104 is preferably 2 inches or 5 cc long (from the point indicated by arrow 106). That is, the curved end 104 is prferably about 11.5% of the overall length of body portion 102. The degree of curvature is such so as not to make it difficult to remove stylet 100 from tube 80 once tube 80 has been inserted into the chest cavity.

The stylet 100 thus is used with thoracic tube 80 as seen in FIG. 5. Stylet 100 extends through tube 80 and into the pleural cavity 111 past the space 112 between ribs 113,114. The stylet 100, since it is curved, may be turned within tube 110 while in the pleural cavity. Ball 101 may have indicia 115 thereon (see also FIG. 3) indicating to the surgeon how stylet 100 should be oriented so the curved end 104 can extend up into the upper thorax of the patient or to the posterior portion of the thorax. Thus, tube 80 can be positioned for either air drainage by pointing curved end 104 up along the wall of the patient's chest or down thereby draining blood from the patient.

It can be seen that I have described a curved stylet and combination thereof which can be used with the curved needle halves of my copending application or with a conventional thoracic tube to carry out thoracic operations. The stylet may have a conventional ball connector for coupling the same to a conventional leur adapter so that a conventional syring may be connected thereto.

The apparatus is particularly suitable for performing thoracostomies. In this operation, negative air pressure in the chest cavities creates special problems. In such operations, it is difficult to remove the trocar and chest tube. The flesh or walls of the puncture grasp the chest tube and make it difficult to remove the holder for the tube so that the wound surrounding the tube can be sutured. There is thus described an improved surgical device for performing thoracostomies where the holder for the tube can be easily removed without the need for removing or disturbing the tube and the stylet is curved for easy entry and withdrawal.

Although I have described a special embodiment of the invention, the invention herein is capable of being carried out in other ways and is only to be limited by the appended claims.

I claim:

1. Surgical apparatus for performing thoracostomies comprising:
    a pair of upper and lower handle portions removably secured together, each of said handle portions having an elongated handle at one end and a planar extension portion at the other end, each of said extension portions having a generally semi-circular opening therethrough on one side thereof, said handle portions being independent of each other and adapted to abut against each other so that said handles extend in a direction substantially parallel to each other but spaced therefrom with said extension portions abutting against each other such that said semi-circular openings abut against each other with said opening forming a generally circular opening;
    each of said handle portions having a flange intermediate said handle and said extension portion, each of said flanges having an opening therethrough, said last mentioned openings being adapted to coincide with each other to form a single opening through said flanges when said portions are abutted against each other as heretofore stated;
    a key member removably mounted in said single opening, said key member and said openings in said flanges having key means therein keying said key member within said single opening so that said key member can quickly and easily non-resiliently lock said handle portions together or be removable therefrom upon rotation thereof to release said handle portions from engagement with each other, said key member and said key means comprising the sole means retaining said handle portions together;
    a curved needle half secured to each extension portion extending downwardly from said semi-circular opening, each of said needle halves having an inner groove terminating at their terminal ends in sharp edges, each of said grooves being aligned with its respective semi-circular opening so that, when said handle portions abut against each other as heretofore stated, said needle halve form a generally circular channel communicating at one end with the exterior of said extension portions and at the other end with said sharp edges; and
    a sytlet having an elongated body terminating in a curved end disposed between said curved needle halves and generally conforming thereto.

2. In the apparatus of claim 1 wherein a flexible chest tube is disposed between said needle halves and retained therein, said curved stylet extending down through said tube.

3. In the apparatus of claim 1 wherein the curved stylet includes connection means at one end for connecting said stylet to a leur adapter, said elongated body including a first straight main body portion extending from said connection means terminating in said curved end having a pointed terminal end.

4. In the apparatus of claim 3 wherein the overall length of curvature of said curved end is about 11.5% of the overall combined length of said main body portion and said curved portion.

5. In the apparatus of claim 3 wherein the degree of curvature of said curved end is between about 5 to 55 degrees with the central longitudinal axis of said main body portion.

6. In the apparatus of claim 5 wherein said degree of curvature is about 35 degrees.

7. In the apparatus of claim 3 wherein the overall length of said straight main body portion is about 17 inches and the overall length of said curved end is about 2 inches.

8. In the apparatus of claim 3 wherein said connection means includes indicia thereon adapted to indicate the direction in which said curved end curves.

* * * * *